United States Patent [19]

Stach et al.

[11] 4,187,890
[45] Feb. 12, 1978

[54] FILLING APPARATUS FOR PHARMACEUTICALS

[75] Inventors: Paul E. Stach; Thomas P. Sherrin, both of Columbus, Ohio

[73] Assignee: Mono-Med, Inc., Columbus, Ohio

[21] Appl. No.: 966,364

[22] Filed: Dec. 4, 1978

[51] Int. Cl.² ............................................. B65B 3/32
[52] U.S. Cl. ...................................... 141/27; 141/94; 222/309
[58] Field of Search ............... 73/425.6; 92/13.5, 13.8, 92/129, 132; 141/2, 18, 21, 25–27, 94, 95, 258; 128/218 A, 218 F, DIG. 1; 222/309, 340, 372

[56] References Cited

U.S. PATENT DOCUMENTS

| 2,896,621 | 1/1959 | Rodrigues | 128/DIG. 1 |
| 3,279,653 | 10/1966 | Pfleger | 128/DIG. 1 |
| 3,935,883 | 2/1976 | Stach et al. | 141/27 |

*Primary Examiner*—Frederick R. Schmidt
*Attorney, Agent, or Firm*—Frank H. Foster

[57] ABSTRACT

An apparatus for filling relatively smaller containers with measured amounts of liquid from a bulk container. A motor drive means (24) is mounted to a support frame for periodically operating a pumping syringe (30). A dual check valve (32) is connected to permit fluid flow from a bulk source (34) into the pumping syringe (30) and from the pumping syringe (30) to a relatively smaller receiving container (36). A clamping means (38) is mounted to the support frame for releasably retaining the outer cylinder member (52) of the pumping syringe (30) in a vertical orientation with its Lure connector uppermost. A gripper means (58) is slideably mounted to the support frame below the clamping means (38) for linear reciprocation parallel to the axis of the pumping syringe (30) and is releasably attached to the piston member of the pumping syringe (30). A cam follower (74) is attached to the gripper means and a biasing means, such as the tension spring (80), is attached to the support frame and the gripper means for urging the piston member downwardly. A rotatably driven cam (84) cyclically and alternately raises the piston member against the urging of the spring (80) and permits it to be lowered by the spring (80). An adjustable stop means (76) is engagable by the gripper means (58) at a selected level below the top dead center of the stroke of the piston member for controlling the volume pumped by the pumping syringe (30) during each cycle of the rotatable cam (84).

6 Claims, 5 Drawing Figures

FILLING APPARATUS FOR PHARMACEUTICALS

TECHNICAL FIELD

This invention relates generally to apparatus for the filling of syringes, vials, IV containers, and other medically useful receptacles with accurately metered quantities of pharmaceuticals and medications from a bulk source. The invention is particularly useful in hospital pharmacies for conveniently transferring unit dosages of a medical fluid from a bulk container to a large number of smaller containers.

BACKGROUND ART

Pharmacies which serve hospitals are required to fill many disposable unit dosage syringes or other medical containers or receptacles with identical quantities of an identical medical fluid. It is important that a high degree of accuracy and cleanliness or sterility be maintained in this procedure. A high productivity rate is also desirable along with the high standards of cleanliness and accuracy in order to most efficiently use pharmacy personnel and minimize cost without sacrificing quality.

Conventionally, this work is performed in a laminar flow environment and is often done entirely manually by piercing the needle of a unit dosage syringe through the resilient top of a bulk container and withdrawing the desired volume of fluid.

Prior art devices to aid in the manual filling of syringes include those shown in U.S. Pat. Nos. 3,602,272 and 3,734,147. More advanced devices, such as those shown in U.S. Pat. No. 3,197,285 and our prior U.S. Pat. No. 3,935,883, show crank-type filling machines. U.S. Pat. Nos. 3,,182,692 and 3,292,667 show other filling devices.

The manual or semi-manual apparatus are, of course, inefficient for filling relatively large numbers of containers. While they require a minimum of investment, they also require tedious and extensive manual manipulation and depend upon visual determination and estimation of the proper dosage volume. They are, therefore, slow and labor intensive.

The prior art systems of others are often so bulky that they interrupt the laminar flow of the controlled environment so that it is no longer aseptic. Further, such systems often use fluid conducting elements which are designed for a unique mechanical function on the particular machine. They must be reused and therefore require disassembly, a thorough cleansing, sterilization and subsequent sterile reassembly for reuse.

DISCLOSURE OF THE INVENTION

The present invention has none of the above disadvantages and additionally uses disposable parts including a pumping syringe which can be easily and conveniently manually purged of air at the begining of the machine operation. Additionally, the dosage volume may be more easily and more accurately selected with embodiments of the present invention.

In summary, the invention is an apparatus for filling relatively smaller containers with measured amounts of liquid from a bulk containers. The apparatus has a support frame, a motor drive means mounted to the support frame, a motor drive control circuit, a pumping syringe, a first check valve connected to permit fluid flow from the bulk source to the Luer fitting of the pumping syringe and a second check valve connected to permit fluid flow from the Luer fitting to the relatively smaller receiving container. In particular, an apparatus in accordance with the present invention has a clamping means mounted to the support frame for releasably retaining the outer cylinder member of the pumping syringe in a vertical orientation with its Luer connector uppermost. A gripper means is slideably mounted to the support frame below the clamping means for linear reciprocation parallel to the axis of the pumping syringe. The gripper means is releasably attachable to the piston member of the pumping syringe. A cam follower is also attached to the gripper means and a biasing means, such as a tension spring, is attached to the frame and to the gripper means for urging the piston member downwardly tending to increase the volume of the pumping syringe. A rotatable cam is drivingly connected to the motor drive means and is engagable with the cam follower for cyclically and alternately raising the piston member against the urging of the biasing means to a top dead center position and then permitting it to be lowered by the urging of the biasing means. An adjustable stop means, which is capable of being engaged by the gripper means at a selected level below the top dead center position, is provided for controlling the stroke of the syringe and thereby controlling the volume pumped by the device during each cycle of the rotatable cam.

BEST MODE FOR CARRYING OUT THE INVENTION

Figure 1:
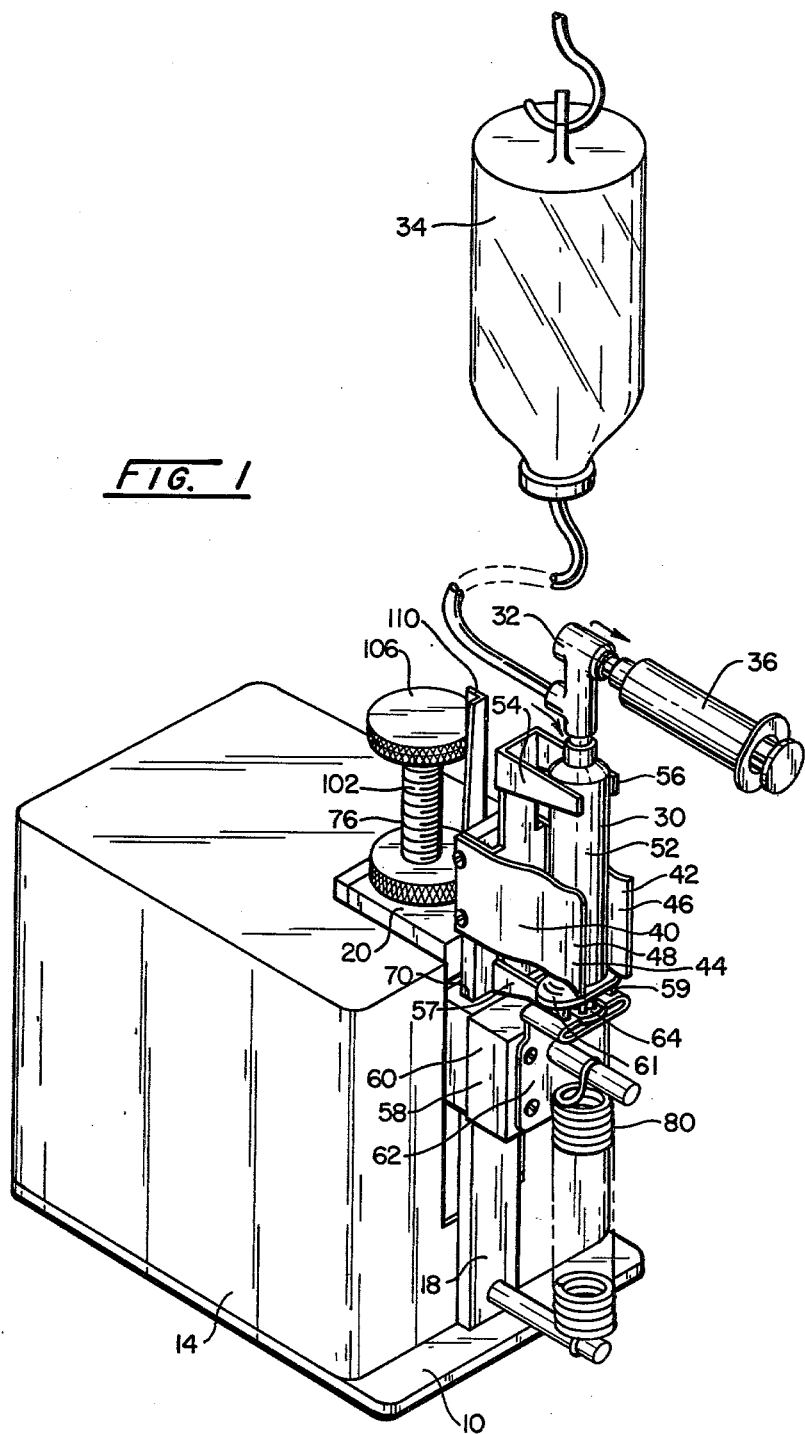
FIG. 1 is a view in perspective of a preferred embodiment of the invention arranged for filling a unit dose syringe.

Referring to the figures, the preferred embodiment of the invention has a support frame including a base 10 having four resilient, nonscratch, anti-friction feet, such as foot 12 and a control panel 14 forming one wall of its outer cabinet. A pair of vertical support walls 16 and 18 are fixed to the base 10 and are connected together at their top by a cross support 20. The support frame also includes a vertical mounting panel 22 fixed to the base 10. An electric motor is mounted to the panel 24 and is drivingly connected to a speed reduction transmission 26.

A motor control circuit 28 is mounted to the rear surface of the control panel 14 with the appropriate switches mounted for access on the opposite (not visible) exterior surface of the control panel 14. The details of the motor control circuit 28 are not illustrated because the circuit is identical to the motor control circuit which is described in our prior U.S. Pat. No. 3,935,883.

A pumping syringe 30 is mounted to the support frame and has a dual check valve 32 mounted to its Luer fitting. This dual check valve 32 may be identical to that illustrated in our prior U.S. Pat. No. 3,935,883. In particular, it has two check valves, one of which is connected to permit fluid flow from a bulk source 34 of medical liquid through the Luer fitting and into the pumping syringe 30. The second check valve is arranged to permit fluid flow from the pumping syringe 30 through its Luer fitting to a relatively smaller receiving container such as the unit dosage syringe 36.

The pumping syringe 30 is releasely retained in a vertical orientation with its Luer connector uppermost by means of a clamping means 38 which is fixed to the vertical support wall 18. The clamping means 38 includes a pair of symmetrically opposed, resiliently deflectable spring clips 40 and 42 which include outwardly turned deflector guides 44 and 46 and cylindrically curved clamping portions 48 and 50 for conformingly seating against the outer surface of the outer cylinder member 52 of the pumping syringe 30. A pair of retaining legs 54 and 56 extend forwardly on opposite sides of the pumping syringe 30 for supporting it against lateral movement. A pair of stop arms 57 and 59 extend forwardly, immediately below the end flange 61 of the cylinder member 52 of the pumping syringe 30 for retaining the flange 61 between the spring clips 40 and 42 and the stop arms 57 and 59. This accurately positions the cylinder member 52 and prevents vertical movement during the pumping cycle.

A gripper means 58 is formed by a nylon block 60 and a metallic bracket 62 which is fixed thereto and which is releaseably attachable to the piston member 64 of the pumping syringe 30. The bracket 62 includes a forwardly extending web with overturned sides to form a track into which slides the thumb seat at the end of the piston member 64.

Therefore, the entire pumping syringe 30 is mounted on the embodiment illustrated in the figures by merely sliding it rearwardly with the outer cylinder member sliding into the clamping means 40 and the outer end of the piston member sliding into the bracket 62. The entire gripper means 58 is mounted to the vertical support wall 18 for linear reciprocation parallel to the axis of the pumping syringe 30. In particular, the vertical support wall 18 has a rectangular cross section which fits into a T-groove 70 formed in the rear of the nylon block 60.

A rod 72 is also fixed to the gripper means 58 and extends from it both forwardly and rearwardly. A slot 73 is cut through the vertical support wall 18 to allow the non-interfering passage of the rod 72. A rotatable bearing 74 is mounted to the rearwardly projecting portion of the rod 72 to form a cam follower which is attached to the gripper means 58. However, the rod 72 projects beyond the bearing 74 so that it may at times engage an adjustable stop means 76.

The forwardly extending portion of the rod 72 is engaged by the hooked upper end of the tension spring 80. The opposite end of the tension spring 80 engages a forwardly extending rod 82 which is fixed to the lower portion of the support wall 18. The spring forms a biasing means attached between the support frame and the gripper means 58 for urging the piston member of the pumping syringe 30 downwardly in a direction which tends to increase the internal volume of the pumping syringe 30.

A rotatable cam 84 is drivingly connected to the motor drive means 24 and is engagable with the cam follower bearing 74. The cam 84 is a circular, eccentrically rotatable plate which is fixed to a sleeve 86 and a rotatable axle 88. The axle 88 is journalled to bearings in the support wall 16 and mounting panel 22 and has a relatively larger drive gear 90 fixed thereto. The drive gear 90 meshes with a relatively smaller drive gear 92 which is connected through a drive shaft 94 to the spaced reduction transmission 26.

As the cam 84 rotates about the axis of the axle 88, it alternately and cyclically raises the cam follower bearing 74, and therefore the piston member 64 of the pumping syringe 30, against the urging of the spring 80 biasing means to a top dead center position which is illustrated in figures and then permits the entire gripper means 58, and therefore the piston member 64 of the pumping syringe 30, to be lowered by the urging of the spring 80 biasing means.

However, the stroke of the linear reciprocation of the gripper means 58 and therefore of the piston member 64 of the pumping syringe 30 is controlled by an adjustable stop means 76. The adjustable stop means 76 is arranged to be engaged by the gripper means 58, and particularly by the rearward end of the rod 72, at a selected level below the top dead center position.

The adjustable stop means 76 comprises a threaded rod 102 which is threadedly engaged to the cross support 20 of the support frame and is oriented substantially parallel to the pumping syringe 30. An annular flange 104 is fixed to the lower end of the threaded rod 102 and extends for engagement, at times, by the rod 72 projecting rearwardly from the gripping means 58. A knurled knob 106 is fixed to the upper end of the threaded rod 102 to facilitate manual grasping and rotation of the threaded rod 102.

A locking means is formed by a knurled lock nut 108 which is also threadedly engaged to the threaded rod 102 to prevent rotation of the threaded rod 102 except when the stop means 76 is being adjusted.

A vertical strut 110 extends vertically upwardly from the cross support 20 and has a scale 112 marked thereon. The scale 112 directly corresponds to the scale conventionally imprinted on the pumping syringe 30. A narrow, annular groove 114 is advantageously formed on the adjustment knob 106 for registration along the scale 112 to indicate the selected volume.

In the operation of the preferred embodiment for filling syringes, a disposable pumping syringe is mounted to the apparatus and connected to the bulk source 34 and the dual check valve 32 as illustrated in FIG. 1. Unlike the device in accordance with our U.S. Pat No. 3,935,833, no purging of the tubing or the pumping syringe need be done prior to connecting the device as illustrated.

Figure 2:
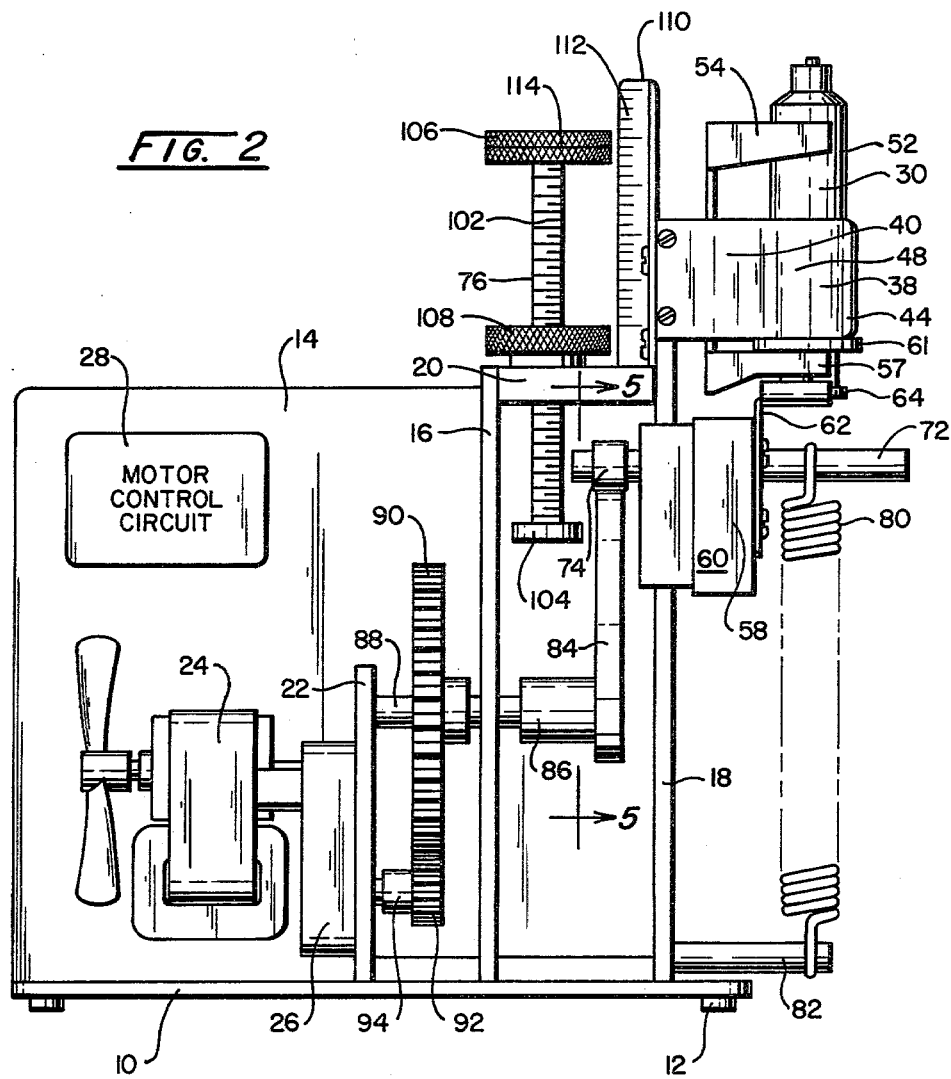
FIG. 2 is a view in side elevation of the embodiment of FIG. 1 with the side, rear and top walls of the cabinet removed to expose the interior.
Figure 3:
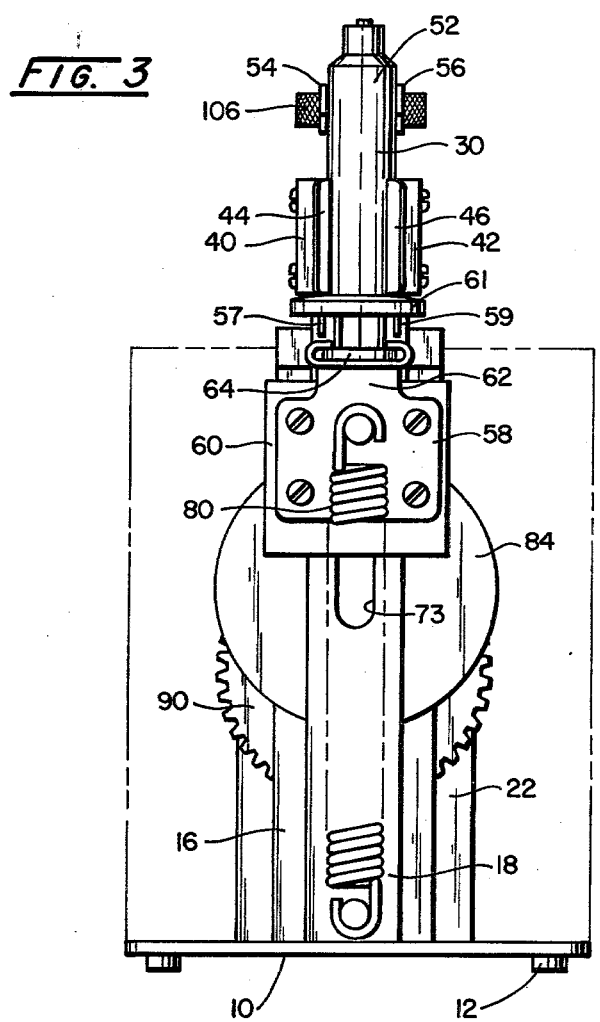
FIG. 3 is a view in front elevation of the embodiment of the invention illustrated in FIG. 1.
Figure 4:
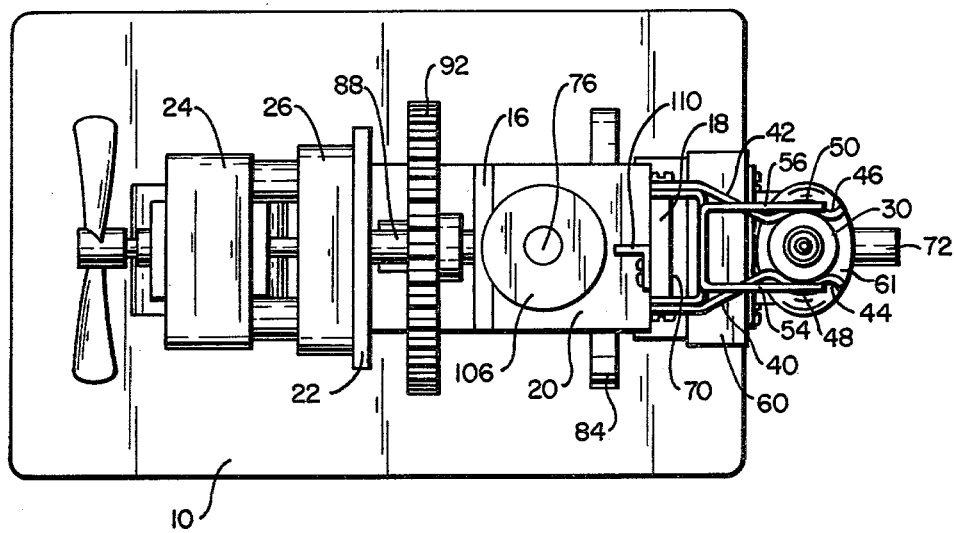
FIG. 4 is a top plan view of the embodiment of the invention illustrated in FIG. 1.
Figure 5:
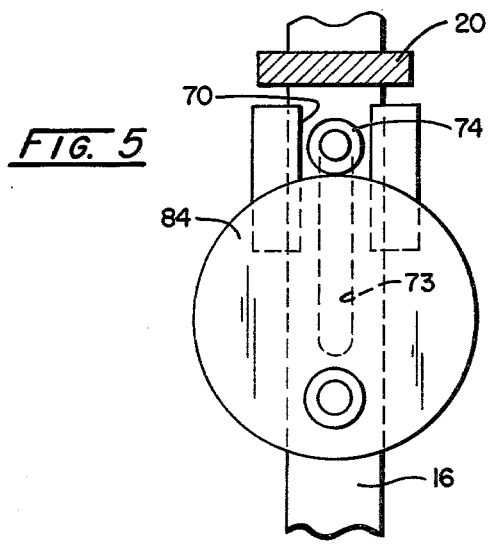
FIG. 5 is a view in vertical section taken along the lines 5—5 of FIG. 2 illustrating the details of the cam and cam follower of the present invention.

As explained in our above prior patent, the electrical control circuit provides two modes of operation. In the first mode a foot pedal control switch may be depressed and the motor will continue running and therefore the cam will continue rotating until the foot is removed from the pedal. In the second mode of operation depression of the pedal causes one complete rotation or one cycle of the cam 84 from the top dead center position illustrated in FIG. 2 through 360° of rotation to return to the same position. Another 360° cycle will occur after release and redepression of the pedal.

Therefore, after assembly of the component parts the foot pedal may be operated in the first mode to rotate the cam 184 180° from the position illustrated in the figures so that the gripper means 58 may be lowered.

The scale 112 is arranged so that zero on the scale will be aligned with the narrow groove 114 on the knurled adjustment knob 106 when the flange 104 of the adjustable stop means 76 supports the rearwardly extending portion of rod 72 at the top dead center position illustrated in the figures. In order to select and adjust the volume to be pumped through the pumping syringe for each cycle, the lock nut 108 is loosened and the adjustment knob 106 is rotated until its annular groove 114 is aligned with the graduation corresponding to the desired dose. After the groove 114 is aligned with the appropriate graduation on a scale 112, the lock nut is again tightened to position the flange 104 an appropriate distance below the top dead center position of the gripper means 58.

With the cam 84 still lowered, the forwardly projecting portion of the rod 72 may be manually grasped and raised against the bias spring 80 and then gradually released to permit the spring to lower it again. This motion may be manually repeated to cause a manually induced pumping action of the pumping syringe 30. This pumping will be continued until all air is expelled from the lines and the pumping syringe and until medical fluid just begins to be emitted from the dual check valve 32. Air within the pumping syringe 30 will be expelled because the pumping syringe is in its inverted position with the Luer fitting at its upper most end. Because the system may be purged after it is mounted in the position for operation, less manipulation of the fluid path is required and waste of precious pharmaceutical liquids is minimized.

The apparatus is then operated in its second mode wherein each 360° rotation of the cam permits the gripper means 58 to descend an amount sufficient to permit only the selected volume of liquid to be drawn into the syringe and then expelled therefrom upon ascent and pumped into the unit dose syringe 36.

The volume adjustment scale of the present invention is more accurate than those used on the crank-type devices because the graduations are spaced twice as far apart. This is because the stroke of the pumping syringe or other pump on a crank-type device will be increased by twice the amount of any increase in the radius of the crank.

The embodiment of the present invention may be also used for filling substances into IV containers. For this purpose the unit dose syringe 36 would be replaced by a length of disposable IV tubing having a hypodermic needle at one end and a Luer fitting on its opposite end. The needle would be inserted in the IV container and the apparatus of the present invention may be cycled multiple times in order to dispense a need IV solution into the IV container. Thus, for example, if 100 cc's were needed in an IV container, then ten cycles, each pumping 10 cc's, would accurately fill the IV container.

Other types of medical containers, even those not requiring a sterile environment, may be filled in accordance with the present invention. A length of disposable IV tubing with a Luer fitting may be connected to the dual check valve 32 in place of the unit dose syringe 36. The opposite open end of the tubing may be manually held above the open mouth of other types of containers. This may, for example, be used for filling respiratory therapy units with inhalants, and non-sterile medications.

We claim:
1. An apparatus for use in filling relatively smaller containers with measured amounts of a liquid from a bulk container, the apparatus including a support frame, a motor drive means mounted to the support frame, a motor drive control circuit, a pumping syringe, a first check valve connected to permit fluid flow from said bulk source to the Luer fitting of said pumping syringe and a second check valve connected to permit fluid flow from said Luer fitting to said relatively smaller receiving container, said apparatus comprising:
  (a) clamping means mounted to said support frame for releasably retaining the outer cylinder member of a pumping syringe in a vertical orientation with its Luer connector uppermost;
  (b) gripper means slideably mounted to said frame below said clamping means for linear reciprocation parallel to the axis of said pumping syringe and releasably attachable to the piston member of said pumping syringe;
  (c) a cam follower attached to said gripper means;
  (d) biasing means attached to said frame and said gripper means for urging said piston member downwardly toward increasing the volume of said syringe;
  (e) a rotatable cam drivingly connected to said motor drive means and engagable with said cam follower for cyclically, alternately raising said piston member against the urging of said biasing means to a top dead center position and permitting it to be lowered by the urging of said biasing means; and
  (f) adjustable stop means for being engaged by said gripper means at a selected level below said top dead center position for controlling the stroke of said syringe.

2. An apparatus in accordance with claim 1 wherein a projection is fixed to said gripper means and wherein said stop means comprises a threaded rod threadedly engaged to said frame substantially parallel to said pumping syringe, said rod having an annular flange for engagement by said projection at its lower end, a knob fixed to its upper end and locking means for releasably preventing its rotation, whereby the stroke of said pumping syringe may be selected by adjustable rotation of said rod.

3. An apparatus in accordance with claim 2 wherein a scale is fixed to said frame adjacent to said knob for indicating the syringe volume change of a selected stroke.

4. An apparatus in accordance with claim 2 wherein said cam follower comprises a rotatable bearing mounted to said projection and interposed between said gripping means and the portion of said projection which is engagable with said stop means.

5. An apparatus in accordance with claim 2 wherein said locking means comprises a lock nut, threadedly engaged to said threaded rod between said knob and said support frame.

6. An apparatus in accordance with claim 1 wherein said cam is a circular, eccentrically rotatable plate.

* * * * *

UNITED STATES PATENT OFFICE
CERTIFICATE OF CORRECTION

PATENT NO. : 4,187,890

DATED : February 12, 1980

INVENTOR(S) : Paul E. Stach and Thomas P. Sherrin

It is certified that error appears in the above-identified patent and that said Letters Patent are hereby corrected as shown below:

The date of issuance should be shown as:

February 12, 1980

Signed and Sealed this

Twenty-seventh Day of May 1980

[SEAL]

Attest:

SIDNEY A. DIAMOND

Attesting Officer

Commissioner of Patents and Trademarks